United States Patent
Ezoe et al.

(10) Patent No.: US 9,346,775 B2
(45) Date of Patent: May 24, 2016

(54) METHOD FOR MANUFACTRURING β-(METH)ACRYLOYLOXY-γ-BUTYRO-LACTONES

(71) Applicant: JNC CORPORATION, Tokyo (JP)

(72) Inventors: Akihiro Ezoe, Berlin (DE); Hideki Hayashi, Kumamoto (JP); Shunji Oshima, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 14/404,951

(22) PCT Filed: Apr. 23, 2013

(86) PCT No.: PCT/JP2013/061886
§ 371 (c)(1),
(2) Date: Dec. 2, 2014

(87) PCT Pub. No.: WO2013/183380
PCT Pub. Date: Dec. 12, 2013

(65) Prior Publication Data
US 2015/0126753 A1  May 7, 2015

(30) Foreign Application Priority Data

Jun. 4, 2012 (JP) .................. 2012-126956

(51) Int. Cl.
C07D 307/00 (2006.01)
C07D 307/33 (2006.01)
C08F 220/28 (2006.01)

(52) U.S. Cl.
CPC ............ *C07D 307/33* (2013.01); *C08F 220/28* (2013.01)

(58) Field of Classification Search
CPC .................................................... C07D 307/33
USPC ........................................................ 549/318
See application file for complete search history.

(56) References Cited

U.S. PATENT DOCUMENTS

| | | | |
|---|---|---|---|
| 6,239,311 B1 | 5/2001 | Hollingsworth | |
| 6,440,636 B1 * | 8/2002 | Ushirogouchi et al. | ... 430/270.1 |
| 6,692,889 B1 | 2/2004 | Funaki et al. | |
| 2003/0078354 A1 | 4/2003 | Medina et al. | |
| 2004/0024228 A1 | 2/2004 | Ishii et al. | |

FOREIGN PATENT DOCUMENTS

| | | |
|---|---|---|
| EP | 0856773 | 8/1998 |
| JP | 47-025065 | 7/1972 |
| JP | 10-212283 | 8/1998 |
| JP | 10-274852 | 10/1998 |
| JP | 11-228560 | 8/1999 |
| JP | 2000-344758 | 12/2000 |
| JP | 2001-48931 | 2/2001 |
| JP | 2001-048933 | 2/2001 |
| WO | 02/06262 | 1/2002 |
| WO | 02/068527 | 9/2002 |
| WO | 2007/106329 | 9/2007 |
| WO | 2012/046770 | 4/2012 |

OTHER PUBLICATIONS

Nozaki et al, "New Protective Groups in Alicyclic Methacrylate Polymers for 193-nm Resists", Journal of Photopolymer Science and technology, Jun. 1997, pp. 545-550, vol. 10, No. 4.

Mulzer et al., "Relative Migratory Aptitude of Substituents and Stereochemistry of Dyotropic Ring Enlargement of β-Lactones", Angewandte Chemie International Edition in English, Aug. 1997, pp. 1476-1478, vol. 36, Issue 13-14.

"International Search Report (Form PCT/ISA/210)", mailed on May 21, 2013, pp. 1-4, in which four of the listed references JP10-212283, JP11-228560, JP2001-048933 and WO02/068527) were cited.

"Office Action of China Counterpart Application", issued on Dec. 4, 2015, pp. 1-16, with English translation . thereof.

SRN-Registry Database, "Chemical Abstracts Service RN: 130224-95-2, 130225-01-3, 195000-63-6, 324761-23-1, 324761-25-3, 324761-27-5, 324761-31-1, 324771-09-7, 325991-18-2, 325991-19-3, 325991-64-8, 325991-67-1, 392309-71-6, 392309-81-8, 521291-57-6, 521291-59-8, 948589-53-5", issued on Sep. 28, 2007.

\* cited by examiner

*Primary Examiner* — Nizal Chandrakumar
(74) *Attorney, Agent, or Firm* — Jianq Chyun IP Office (57) ABSTRACT

The art relates to provision of a method for manufacturing an (meth)acrylic polymerizable monomer that can be used in various applications, such as an optical material, a resist material, a coating material and a laminate material, and provision of a new β-(meth)acryloyloxy-γ-butyrolactone compound by applying the manufacturing method. The method for manufacturing the β-(meth)acryloyloxy-γ-butyrolactone compound is described, in which a (meth)acrylate compound having a carbonyl group and a ketene compound are condensed and isomerized. Further, the manufacturing method is applied to the new β-(meth)acryloyloxy-γ-butyrolactone compound.

2 Claims, 2 Drawing Sheets

METHOD FOR MANUFACTRURING β-(METH)ACRYLOYLOXY-γ-BUTYRO-LACTONES

CROSS-REFERENCE TO RELATED APPLICATIONS

This application is a 371 application of an international PCT application serial no. PCT/JP2013/061886, filed on Apr. 23, 2013, which claims the priority benefit of Japan application no. 2012-126956, filed on Jun. 4, 2012. The entirety of each of the above mentioned patent applications is hereby incorporated by reference herein and made a part of this specification.

TECHNICAL FIELD

The present invention relates to a method for manufacturing β-(meth)acryloyloxy-γ-butyrolactones being one kind of 5-membered ring lactone-based (meth)acrylate compound, and a β-(meth)acryloyloxy-γ-butyrolactone compound obtained by the manufacturing method.

BACKGROUND ART

A (meth)acrylate compound is copolymerized with any other polymerizable monomer, and is used in various applications, such as an optical material, a resist material, a coating material and a laminate material. The resist material is widely used in a process in which patterning is conducted by photolithography to perform microprocessing, or the like, such as manufacture of a printed circuit board, a liquid crystal display panel and a semiconductor device. In particular, in the process of photolithography for manufacturing the semiconductor device, study has been conducted on short wavelength exposure for shortening an exposure wavelength to increase resolution in order to allow further microprocessing, and study has been actively conducted on a chemical amplification type resist material in correspondence to the short wavelength exposure.

The chemical amplification type resist material is mainly provided as a structure formed by combining a polymer component obtained by copolymerizing a plurality of polymerizable monomers such as a (meth)acrylate compound, a photoacid generator that is exposed to an exposure light source to change solubility of the polymer component, a solvent and so forth. The resist material is required to satisfy characteristics such as application properties, adhesion, treatment resistance, developability and solubility, and also to satisfy characteristics related to an exposure wavelength, such as light transmittance and light sensitivity.

The polymer component is required to have high transmittance at the exposure wavelength, to cause a deprotection reaction in an exposed portion by acid generated from the photoacid generator after exposure to solubilize or conversely insolubilize the portion in an alkali liquid developer, to have good adhesion and etching-resistant properties of a resist, and simultaneously to satisfy lithography characteristics such as reduction of roughness of the resulting resist pattern and fluctuation of pattern width, and resistance to a pattern collapse in association with a demand for achieving a fine resist pattern. In order to balance the characteristics, the polymer component obtained by copolymerizing a plurality of polymerizable monomers is used.

For example, polymer components are combined and used in which the polymer components are obtained by copolymerizing a polymerizable monomer such as a lactone-based (meth)acrylate compound in which the light transmittance is high at the exposure wavelength and the adhesion properties is good, a polymerizable monomer having an adamantane skeleton, a norbornane skeleton or alicyclic skeleton in which the light transmittance is high at the exposure wavelength and etching resistance is good, a polymerizable monomer that is decomposed by the acid generator to be alkali-soluble, an alkali-soluble polymerizable monomer and so forth.

Study has been actively conducted toward realization of a chemical amplification type resist material having well-balanced characteristics by developing various kinds of polymerizable compounds such as a compound having a 6-membered ring lactone (δ-valerolactone) skeleton as the lactone-based (meth)acrylate compound, a compound having a 5-membered ring lactone (γ-butyrolactone) skeleton, a compound having a skeleton in which norbornane and lactone form a condensed ring, and a compound having cyclohexane lactone ring structure, and incorporating the compounds as the polymer components.

As the (meth)acrylate compound having the 5-membered ring lactone (γ-butyrolactone) skeleton, α-(meth)acryloyloxy-γ-butyrolactones (Patent literature No. 1) and β-(meth)acryloyloxy-γ-butyrolactones (Patent literature No. 2) are known. In particular, α-(meth)acryloyloxy-γ-butyrolactones that have a substituent at an α-position are industrially provided, and usefully used for a chemical amplification-type resist composition. On the other hand, β-(meth)acryloyloxy-γ-butyrolactones are difficult to industrially manufacture, industrial use of which is limited, and no synthesis has been made until now depending on structure of the compound.

The β-(meth)acryloyloxy-γ-butyrolactones are known to be further excellent in deprotection reaction characteristics by acid and lithography characteristics in comparison with the α-(meth)acryloyloxy-γ-butyrolactones, and establishment of a method by which the β-(meth)acryloyloxy-γ-butyrolactones can be industrially and inexpensively manufactured is required (Non-patent literature No. 1).

With regard to the β-(meth)acryloyloxy-γ-butyrolactones and a method for manufacturing the same, a method is known in which β-hydroxy-γ-butyrolactones are obtained to be esterified with (meth)acrylic acid chloride or (meth)acrylic acid, or transesterified with (meth)acrylate (Patent literature No. 2), and a method is also known in which (meth)acrylic acid is allowed to react with halo-γ-butyrolactones (Patent literature No. 3). All of the manufacturing methods include a method for manufacturing a compound having a hydroxy group or a halogen group at a β-position of a γ-butyrolactone ring to manufacture the compound by an esterification reaction with (meth)acrylic acid or a derivative thereof.

As a method for manufacturing the compound having the hydroxy group at the β-position of the γ-butyrolactone ring, such methods are known as a method for esterifying halide bromoacetate with hydroxyacetone or 3-hydroxypropionaldehyde to prepare 2-oxopropyl bromoacetate or 2-formylethyl bromoacetate, and to lactonize the resulting product in the presence of a catalyst and to obtain β-hydroxy-β-methyl-γ-butyrolactone or β-hydroxy-γ-butyrolactone (Patent literature No. 2), a method for manufacturing the compound from 3,4-dihydroxybutyric acid (Patent literature Nos. 4 and 7), and a method for manufacturing the compound using (β,γ-unsaturated carboxylic acid as a raw material. (Patent literature No. 5).

In the method for obtaining β-hydroxy-β-methyl-γ-butyrolactone or β-hydroxy-γ-butyrolactone through 2-oxopropyl bromoacetate or 2-formylethyl bromoacetate from esterification of halide bromoacetate, and hydroxyacetone or 3-hydroxypropionaldehyde, a yield in each step is low, pretreatment of zinc powder to be used as a catalyst is required, or the like, and thus the method is difficult to utilize as an industrial manufacturing method.

In the method for manufacturing the compound from 3,4-dihydroxybutyric acid, hydrogen peroxide is used (Patent literature No. 4) or cyanide is used (Patent literature No. 7) in order to manufacture 3,4-dihydroxybutyric acid. Therefore, according to a technique, a substance having a risk of explosion or toxicity should be used.

The method for manufacturing the compound using β,γ-unsaturated carboxylic acid as the raw material is excellent in synthesizing β-hydroxy-γ-butyrolactone in one step by using 3-butenoic acid as the raw material. However, the method also includes a reaction using hydrogen peroxide, and requires suitable process control and waste disposal.

Thus, according to the methods in which the compound having the hydroxy group at the β-position of γ-butyrolactones is previously formed to manufacture the compound by the esterification reaction with (meth)acrylic acid or the derivative thereof as a hydroxy form or a halogen form thereof, a yield in manufacturing a β-hydroxy form compound or a β-halogen form compound of γ-butyrolactones is low, manufacturing conditions are tough, synthesis of a starting material is required due to incapability of industrially utilizing the material and so forth, and therefore the compound is difficult to manufacture in bulk and inexpensively. As a result, the β-(meth)acryloyloxy-γ-butyrolactones have had a problem of incapability of industrially manufacturing the compound inexpensively.

As the method for forming the γ-butyrolactone skeleton, a compound having a β-propiolactone skeleton is known to be isomerized to form the γ-butyrolactone skeleton (Non-patent literature No. 2). In the case where a hydroxy form compound of γ-butyrolactones is manufactured by applying the above method, manufacture of a hydroxymethyl form compound having the β-propiolactone skeleton corresponding to the hydroxy form compound of γ-butyrolactones is previously required.

As the method for manufacturing the compound having the β-propiolactone skeleton, a method for allowing aliphatic aldehydes to react with ketenes is known (Patent literature No. 6), for example, and application of the method to synthesis of low-molecular-weight lactone having a β-skeleton, such as β-butyrolactone, β-propiolactone and β-caprolactone is disclosed.

However, manufacture of the hydroxy form compound having the β-propiolactone skeleton by applying the method is difficult to industrially execute due to difficulty in manufacture of the compound to be the raw material to cause difficulty in procurement, many side reactions to cause poor reaction selectivity, or the like. Accordingly, industrial manufacture of the β-hydroxy form compound of γ-butyrolactones is still difficult, and as a result, establishment of a new method for industrially manufacturing the β-(meth)acryloyloxy-γ-butyrolactones has been strongly required.

CITATION LIST

Patent Literature

Patent literature No. 1: JP H10-274852 A.
Patent literature No. 2: JP H10-212283 A.
Patent literature No. 3: JP 2000-344758 A.
Patent literature No. 4: U.S. Pat. No. 6,239,311 B.
Patent literature No. 5: WO 02/006262 A.
Patent literature No. 6: JP S47-25065 B.
Patent literature No. 7: JP H11-228560 A.

Non-Patent Literature

Non-patent literature No. 1: Koji Nozaki and Ei Yano, "New Protective Groups in Alicyclic Methacrylate Polymers for 193-nm Resists," Journal of Photopolymer Science and Technology, 1997, 10, 545-550.

Non-patent literature No. 2: Johan Mulzer, et al., "Relative Migratory Aptitude of Substituents and Stereochemistry of Dyotropic Ring Enlargements of β-Lactones," Angew. Chem. Int. Ed. Engl., 1997, 36, 1476-1478.

SUMMARY OF INVENTION

Technical Problem

As described above, an object of the invention is to provide a method for industrially manufacturing β-(meth)acryloyloxy-γ-butyrolactones being one kind of 5-membered ring lactone-based (meth)acrylate compound, and to provide a β-(meth)acryloyloxy-γ-butyrolactone compound to be manufactured by the manufacturing method.

Solution to Problem

In order to attain the object, the present inventors have diligently continued to conduct study, and have found that β-(meth)acryloyloxy-γ-butyrolactones can be efficiently manufactured by forming a (meth)acrylate compound having a β-propiolactone skeleton, and isomerizing the resulting (meth)acrylate compound having the β-propiolactone skeleton, and further found conditions for performing the manufacture in one reaction process to manufacture a variety of β-(meth)acryloyloxy-γ-butyrolactone compounds by applying the method. The invention includes the following structures.

Item 1. A method for manufacturing a β-(meth)acryloyloxy-γ-butyrolactone compound represented by formula (2), wherein a (meth)acrylate compound having a β-propiolactone skeleton as represented by formula (1) is isomerized:

wherein, $R_1$ is hydrogen or methyl, and $R_2$, $R_3$, $R_4$, $R_5$ and $R_6$ are independently hydrogen or alkyl having 1 to 5 carbons.

Item 2. The method for manufacturing the β-(meth)acryloyloxy-γ-butyrolactone compound according to item 1, wherein a (meth)acrylate compound having a carbonyl group as represented by formula (3) and a ketene compound represented by formula (4) are condensed, and the resulting (meth)acrylate compound having the β-propiolactone skeleton is isomerized:

wherein, $R_1$ is hydrogen or methyl, and $R_2$, $R_3$, $R_4$, $R_5$ and $R_6$ are independently hydrogen or alkyl having 1 to 5 carbons.

Item 3. The method for manufacturing the β-(meth)acryloyloxy-γ-butyrolactone compound according to item 2, wherein a reaction for forming the (meth)acrylate compound having the β-propiolactone skeleton as represented by formula (1) according to item 1, and an isomerization reaction for isomerizing the resulting (meth)acrylate compound having the β-propiolactone skeleton to form the β-(meth)acryloyloxy-γ-butyrolactone compound represented by formula (2) according to item 1 are carried out in one reaction process.

Item 4. A β-(meth)acryloyloxy-γ-butyrolactone compound represented by formula (2) obtained by the method for manufacturing the same according to any one of items 1 to 3:

wherein, $R_1$ is hydrogen or methyl, and $R_2$, $R_3$, $R_4$, $R_5$ and $R_6$ are independently hydrogen or alkyl having 1 to 5 carbons.

Item 5. The β-(meth)acryloyloxy-γ-butyrolactone compound represented by formula (2) according to item 4.

Advantageous Effects of Invention

According to a manufacturing method of the invention, industrial manufacture of a β-(meth)acryloyloxy-γ-butyrolactone compound, and the compound can be provided, and the compound can be used as a polymerizable monomer in various applications, such as an optical material, a resist material, a coating material and a laminate material.

Further, the manufacturing method of the invention is applied, and thus various kinds of β-(meth)acryloyloxy-γ-butyrolactone compounds that have not been obtained so far can be obtained. A γ-butyrolactone skeleton has light absorption characteristics suitable for short wavelength exposure, and thus the compounds can be used advantageously for the resist material to be used for short wavelength exposure. The compound is copolymerized and the resulting product is used as a polymer obtained, or the compounds are mixed and the resulting product is used as the polymerizable monomer, and thus such a product can be used for adjustment of compatibility, adjustment of viscosity, adjustment of adhesion, adjustment of solubility or the like of a solution to be used for screen printing or inkjet.

DESCRIPTION OF EMBODIMENTS

The invention will be described in more detail below. The invention concerns a manufacturing method based on isomerizing a (meth)acrylate compound having a β-propiolactone skeleton as represented by formula (1) to form a β-(meth)acryloyloxy-γ-butyrolactone compound represented by formula (2).

Here, $R_1$ is hydrogen or methyl, and $R_2$, $R_3$, $R_4$, $R_5$ and $R_6$ are independently hydrogen or alkyl having 1 to 5 carbons, and further preferably, independently hydrogen or methyl.

The (meth)acrylate compound having the β-propiolactone skeleton according to formula (1) is isomerized by heat energy or the like as shown in a reaction formula described below to form the β-(meth)acryloyloxy-γ-butyrolactone compound according to formula (2).

Here, $R_1$, $R_2$, $R_3$, $R_4$, $R_5$ and $R_6$ are defined in a manner identical with the definitions described above.

A reaction method for allowing isomerization is not particularly limited, but the isomerization can be carried out, for example, by dissolving in a solvent the (meth)acrylate compound having the β-propiolactone skeleton as represented by formula (1), and applying heat to the resulting mixture. When necessary, a catalyst may be added thereto to promote the reaction. As the catalyst, a Lewis acid catalyst, for example, an organic complex compound of boron, and halide of zinc, aluminum, titanium, iron and magnesium are used. Moreover, when necessary, a polymerization inhibitor or the like may be added to the mixture. A reaction temperature for allowing the isomerization depends on a kind of the (meth)acrylate compound having the β-propiolactone skeleton, but the isomerization is preferably carried out ordinarily in a temperature range of 20 to 50° C. Within the temperature range, a higher reaction temperature is preferred because the reaction proceeds faster and a yield is improved. Moreover, a lower reaction temperature is preferred because a side reaction and a polymerization reaction can be suppressed.

The (meth)acrylic acid ester compound having the β-propiolactone skeleton according to formula (1) can be formed, for example, by allowing a ketene compound according to formula (4) to react with a compound having a carbonyl group according to formula (3).

(3)

(4)

Here, $R_1$, $R_2$, $R_3$, $R_4$, $R_5$ and $R_6$ are defined in a manner identical with the definitions described above.

For example, the reaction can be carried out by adding the ketene compound according to formula (4) to a solution in which the compound having the carbonyl group according to formula (3) is dissolved into the solvent, a catalyst is added, and the resulting mixture is cooled, while the solution is stirred to maintain cooling. As the solvent, ethers such as tetrahydrofuran, diethyl ether, di-n-butyl ether, 1,4-dioxane and ethylene glycol dimethyl ether, aliphatic hydrocarbons such as hexane, heptane, octane, cyclohexane and methylcyclohexane, alicyclic hydrocarbons, aromatic hydrocarbons such as benzene, toluene, xylene and ethylbenzene, esters such as methyl acetate, ethyl acetate and n-butyl acetate, halogenated hydrocarbons such as dichloromethane, and nitriles such as acetonitrile and propionitrile can be used alone or mixed and then used.

As the catalyst, halide of metal, for example, halide of zinc, aluminum, titanium and iron, or a organic complex compound of boron halide can be used. In particular, a diethyl ether complex of boron trifluoride can be preferably used due to high reaction selectivity. An amount of addition of the catalyst is preferably in the range of 0.1% by weight to 50% by weight based on a reaction substrate, and further preferably, in the range of 2% by weight to 30% by weight based thereon. Within the range, a higher amount of addition is preferred because the reaction becomes faster and the yield is improved, and a lower amount of addition is preferred because the reaction selectivity can be improved, and a load in a purification step such as catalyst treatment can be reduced.

The compound represented by formula (1) can be obtained by adding the compound represented by formula (4) to the mixture, and then continuing stirring to promote the reaction, washing with alkali and water a reaction crude liquid after completion of the reaction, removing the solvent, and then applying purification treatment such as recrystallization and distillation treatment.

The compound having the carbonyl group according to formula (3) is obtained, for example, by allowing the compound represented by formula (5) to react with the compound represented by formula (6) or formula (7).

Here, $R_1$, $R_2$, $R_3$ and $R_4$ are defined in a manner identical with the definitions described above. X is halogen.

Specific examples of the compound represented by formula (5) include 1-hydroxy-2-propanone, 3-hydroxy-2-butanone, 1-hydroxy-2-butanone, 3-hydroxy-2-pentanone and 2-hydroxyethanal, but are not limited thereto.

As the compound represented by formula (6), dimethacrylic anhydride and diacrylic anhydride are preferably used, and as the compound represented by formula (7), (meth)acrylic acid halides, in particular, (meth)acrylic acid chloride, (meth)acrylic acid bromide and (meth)acrylic acid iodide can be used.

An esterification reaction using the compound represented by formula (5) and the compound represented by formula (6) can be carried out according to an established method. For example, the compound represented by formula (3) is obtained by adding a base such as triethylamine, and a catalyst such as N,N-dimethyl-4-aminopyridine to a solution in which the compound represented by formula (5) and the compound represented by formula (6) are dissolved into the solvent, a polymerization inhibitor is added thereto and the resulting mixture is heated and stirred, allowing reaction therein, and through a purification operation such as washing, concentration and distillation.

An esterification reaction using the compound represented by formula (5) and the compound represented by formula (7) can also be carried out according to the established method. For example, the compound represented by formula (3) is obtained by adding the compound represented by formula (7) to a solution in which the compound represented by formula (5) and a base such as triethylamine are dissolved, a polymerization inhibitor is added thereto and the resulting mixture is cooled and stirred to allow reaction, while cooling is maintained, and through a purification operation such as washing, concentration and distillation.

Ketene being the compound represented by formula (4) is obtained by thermal decomposition of acetone or acetic acid. Monomethyl ketene is obtained by thermal decomposition of diethyl ketone or propionic acid. Moreover, $R_5$-substituted ketene and $R_6$-substituted ketene is formed by allowing metallic zinc to act on acetylbromide subjected to α-substitution with $R_5$, $R_6$ and bromine, or allowing tertiary amine to act on carboxylic acid chloride subjected to α-substitution with $R_5$ and $R_6$. For example, dimethyl ketene can be generated by adding the base such as triethylamine to isobutyryl chloride.

A condensation reaction between the compound having the carbonyl group according to formula (3) and the ketene compound represented by formula (4) includes an exothermic reaction, and therefore carried out while heat is removed. A preferred reaction temperature depends on kinds of the reaction substrate and the ketene compound to be reacted, but is ordinarily in the temperature range of 0 to 50° C. Within the temperature range, a higher reaction temperature is preferred because the reaction proceeds faster and the yield is improved. A lower reaction temperature is preferred because the side reaction and the polymerization reaction can be suppressed.

The (meth)acrylate compound having the β-propiolactone skeleton according to formula (1) is obtained by allowing the ketene compound according to formula (4) to react with the compound having the carbonyl group according to formula (3) while temperature is maintained at a temperature close to a lower limit in a preferred temperature range, for example, 0° C. to 10° C., and applying a purification operation such as washing, concentration and distillation. The β-(meth)acryloyloxy-γ-butyrolactone compound according to formula (2) is obtained by isomerizing the resulting (meth)acrylate compound having the β-propiolactone skeleton according to formula (1) by the method for allowing the isomerization described above.

If the compound having the carbonyl group according to formula (3) and the ketene compound according to formula (4) are allowed to react by maintaining temperature at a temperature close to an upper limit of the preferred temperature range, for example, 20° C. to 50° C., and increasing an amount of addition of a catalyst to a somewhat higher level, for example, 3% by weight to 50% by weight, the reaction of forming the (meth)acrylate compound having the β-propiolactone skeleton according to formula (1) and the isomerization reaction thereof simultaneously proceed, and thus the β-(meth)acryloyloxy-γ-butyrolactone compound according to formula (2) can be formed in one reaction process.

Even from the reaction crude liquid obtained by the reaction according to any manufacturing method, the β-(meth)acryloyloxy-γ-butyrolactone compound according to formula (2) is obtained by applying the purification operation such as washing, concentration and distillation.

For example, β-methacryloyloxy-β-methyl-γ-butyrolactone is obtained by allowing ketene to react with 2-oxopropyl methacrylate, α,β-dimethyl-β-methacryloyloxy-γ-butyrolactone is obtained by allowing methylketene to react with 2-oxopropyl methacrylate, and α,α,β-trimethyl-β-methacryloyloxy-γ-butyrolactone is obtained by allowing dimethylketene to react with 2-oxopropyl methacrylate, respectively. Then, β-methacryloyloxy-γ-butyrolactone is obtained by allowing ketene to react with 2-oxoethyl methacrylate, β-methacryloyloxy-α-methyl-γ-butyrolactone is obtained by allowing methylketene to react with 2-oxoethyl methacrylate, and α,α-dimethyl-β-methacryloyloxy-γ-butyrolactone is obtained by allowing dimethylketene to react with 2-oxoethyl methacrylate, respectively. Moreover, β,γ-dimethyl-β-methacryloyloxy-γ-butyrolactone is obtained by allowing ketene to react with 3-oxobutane-2-yl methacrylate, α,β,γ-trimethyl-β-methacryloyloxy-γ-butyrolactone is obtained by allowing methylketene to react therewith, and α,α,β,γ-tetramethyl-β-methacryloyloxy-γ-butyrolactone is obtained by allowing dimethylketene to react with 3-oxobutane-2-yl methacrylate, respectively.

The β-(meth)acryloyloxy-γ-butyrolactone compound according to formula (2) can be used, for example, as a polymerizable monomer component for a resist material that is directly subjected to patterning as provided by combining a polymer component obtained by copolymerizing the compound with any other polymerizable monomer, a polymerizable monomer component, a polyfunctional polymerizable monomer component, a thermal polymerization initiator or a photopolymerization initiator, a solvent and so forth, or as a polymerizable monomer for a photoresist material as provided by combining a polymer component by copolymerizing the compound with a plurality of polymerizable monomers, a photoacid generator, a solvent and so forth.

Specific examples of the compounds that can be combined or copolymerized with the compound represented by formula (2) include (meth)acrylic acid, a (meth)acrylate monomer, a vinyl ether derivative, a styrene derivative and maleic anhydride. Specific examples of the (meth)acrylate monomers include a compound formed by replacing hydrogen of carboxylic acid of (meth)acrylic acid with methyl, ethyl, n-propyl, i-propyl, n-butyl, i-butyl, t-butyl, cyclopentyl, cyclohexyl, tricyclodecyl[5.2.1.0$^{2,6}$], adamanthyl, norbornyl, isobornyl, hydroxyethyl, propoxyethyl, butoxyethyl, 2-methyl-2-adamanthyl, 2-ethyl-2-adamanthyl, 3-hydroxy-1-adamanthyl, tetrahydropyranyl, methoxytetrahydropyranyl or tetrahydropyranyl. Specific examples of the vinyl ether derivatives include ethyl vinyl ether, cyclohexylvinyl ether and hydroxyethyl vinyl ether. Specific examples of the styrene derivatives include styrene, p-hydroxystyrene, p-methoxystyrene and p-t-butoxystyrene. The copolymerizable compounds can be used alone or in combination of two or more kinds.

A method for obtaining the polymer component by allowing polymerization or copolymerization of the compound represented by formula (2) is not particularly limited, and the polymerization or the copolymerization can be performed by an established method. For example, the polymer component can be obtained by mixing individual compounds to be a desired mole ratio in a solvent, adding a polymerization initiator to allow the polymerization or the copolymerization by heating the resulting mixture or irradiating the mixture with light, separating the resulting product, and when necessary, by applying purification treatment thereto.

EXAMPLES

The invention will be described in more detail by way of Examples below, but the invention is by no means limited to the Examples. In addition, a compound was identified using a proton nuclear magnetic resonance spectrum (hereinafter, referred to as NMR), and a purity of the compound was determined using gas chromatography (hereinafter, referred to as GC) or high performance liquid chromatography (hereinafter, referred to as HPLC). NMR was measured in a CDCl$_3$ solvent and using tetramethylsilane as an internal standard by using JEOL JNM-ECP400 (400 MHz).

Example 1

Synthesis-1 of β-methacryloyloxy-β-methyl-γ-butyrolactone (compound in which $R_1$, $R_2$=methyl, and $R_3$, $R_4$, $R_5$ and $R_6$=hydrogen)

In a 1 L four-necked flask, 50 g of 1-hydroxy-2-propanone (made by Wako Pure Chemical Industries, Ltd., purity: 90.0% or more) was put, and dissolved in 485 g of toluene. Then, 113 g of dimethacrylic anhydride (made by ALDRICH Corporation, purity: 94.0%) and 0.5% by weight of 4,4'-thiobis(6-t-butyl-o-cresol) were added thereto, and a stirrer, a thermometer and a Dimroth cooling tube were connected thereto. Then, 80 g of triethylamine was added dropwise to a solution obtained by stirring the resulting mixture and adjusting solution temperature to 45° C., and further a solution obtained by dissolving 0.75 g of N,N-dimethyl-4-aminopyridine (made by Wako Pure Chemical Industries, Ltd., purity: 99.0% or more) in 15 g of toluene was added dropwise thereto. While the solution temperature was kept in the range of 50 to 70° C., stirring was continued for 90 minutes from start of the dropwise addition, and 70 g of methyl alcohol was added thereto to terminate the reaction. The resulting reaction mixture was washed with 1 N-hydrochloric acid, a 10% sodium carbonate aqueous solution and saturated brine, dried over anhydrous magnesium sulfate and separated by filtration to obtain a reaction crude liquid. After the solvent was removed using an evaporator, the reaction crude liquid was distilled under reduced pressure to give 49.7 g of 2-oxopropyl methacrylate having a GC purity of 99.0% (yield; 51.9% based on 1-hydroxy-2-propanone).

In a 1 L four-necked flask, 200 g of 2-oxopropyl methacrylate obtained by the method described above and 460 g of ethyl acetate were put, and a stirrer, a thermometer, a Dimroth cooling tube and a gas inlet tube were connected thereto. The resulting solution was stirred and solution temperature was adjusted to 30° C. using a water bath, and then 5 mol % of diethyl ether complex of boron trifluoride (made by Kanto Chemical Co., Inc., purity: 95.0% or more) was added thereto based on a substrate. While the solution temperature was kept at 30° C. under stirring, a ketene gas was passed to the solution through the gas inlet tube at a rate of 0.55 equivalent/h based on the substrate, and the reaction was continued until 2-oxopropyl methacrylate disappeared by GC analysis. The reaction was completed in 4.5 hours, blowing of the ketene gas was stopped, and the remaining ketene gas was removed to an outside of the system by passing a nitrogen gas.

Figure 1:
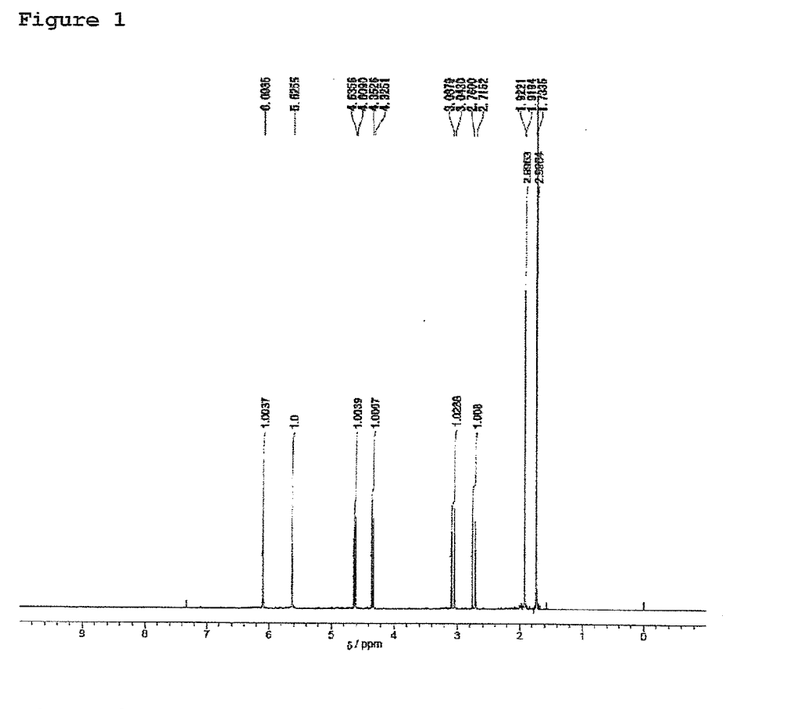
FIG. 1 shows an NMR spectrum of β-methacryloyloxy-β-methyl-γ-butyrolactone obtained by a method in Example 1.

The resulting reaction mixture was washed with a 10% sodium carbonate aqueous solution and saturated brine, and dried over magnesium sulfate. After separation by filtration, the solvent was distilled off using an evaporator to obtain a crude product. The crude product was distilled under reduced pressure to give 107.6 g of β-methacryloyloxy-β-methyl-γ-butyrolactone represented by formula (8) and having a GC purity of 98.2% (yield: 41.5% based on 2-oxopropyl methacrylate). FIG. 1 shows an NMR measurement chart.

(8)

Example 2

Synthesis-2 of β-methacryloyloxy-β-methyl-γ-butyrolactone (compound in which $R_1$, $R_2$=methyl, and $R_3$, $R_4$, $R_5$ and $R_6$=hydrogen)

In a 2 L four-necked flask subjected to replacement with nitrogen, 50 g of 1-hydroxy-2-propanone was put, and dissolved in 700 g of tetrahydrofuran, and a stirrer, a thermometer and a Dimroth cooling tube were connected thereto. After the resulting solution was stirred and cooled to about 5° C., 76.8 g of triethylamine and 25 mg of hydroquinone were added thereto. While the resulting mixture was cooled to about 5° C. under stirring, 71.9 g of methacryloyl chloride (made by Wako Pure Chemical Industries Ltd., purity: 97.0% or more) was slowly added dropwise thereto, and stirring was further continued for 3 hours to carry out an esterification reaction. While the reaction mixture was held at about 5° C., the mixture was acid-washed with 2N-hydrochloric acid, and an extraction operation was performed twice using 300 mL of ethyl acetate to obtain an organic layer. The organic layer was washed with a 10% sodium hydrogen carbonate aqueous solution and saturated brine, dried over anhydrous magnesium sulfate, and separated by filtration to obtain a reaction crude liquid. The solvent was distilled off from the reaction crude liquid using an evaporator to obtain 85.5 g of crude 2-oxopropyl methacrylate. A yield of 2-oxopropyl methacrylate determined from a proton ratio by NMR was 67.1 g (yield: 69.9% based on 1-hydroxy-2-propanone).

The crude 2-oxopropyl methacrylate was provided for a subsequent reaction without purification. In a 300 mL four-necked flask, crude 2-oxopropyl methacrylate containing 44.5 g of 2-oxopropyl methacrylate and 100 g of ethyl acetate were put, and a stirrer, a thermometer, a Dimroth cooling tube and a gas inlet tube were connected thereto. The resulting solution was stirred and cooled to about 5° C. using an ice bath, and 5 mol % of diethyl ether complex of boron trifluoride was added thereto based on a substrate. While solution temperature was kept at 5° C. under stirring, a ketene gas was passed to the solution through a gas inlet tube at a rate of 1.1 equivalent/h based on the substrate, and the reaction was continued until 2-oxopropyl methacrylate disappeared by GC analysis. The reaction ended in 150 minutes, blowing of the ketene gas was stopped, and the remaining ketene was removed to an outside of the system by passing a nitrogen gas.

The resulting reaction mixture was washed with a 10% sodium hydrogen carbonate aqueous solution and saturated brine, and dried over anhydrous magnesium sulfate. After separation by filtration, 20 mg of hydroquinone was added thereto and the solvent was distilled off using an evaporator. The reaction mixture after the solvent was distilled off was purified by column separation using silica gel as a packing agent and a mixed solvent of ethyl acetate and heptane as an eluent. Further, recrystallization was repeated twice using toluene and heptane to give 28.2 g of β-methacryloyloxymethyl-β-methyl-β-propiolactone having a purity of 99.6% represented by formula (8) by HPLC analysis (yield: 48.9% based on 2-oxopropyl methacrylate).

In a 50 mL four-necked flask, 0.5 g of β-methacryloyloxymethyl-β-methyl-β-propiolactone was put, and dissolved in 10 g of ethyl acetate, and a stirrer, a thermometer and a Dimroth cooling tube were connected thereto. Then, 5 mol % of diethyl ether complex of boron trifluoride was added thereto based on the substrate, and 5 mg of p-methoxyphenol was added thereto, and while solution temperature was kept at 30° C., the resulting mixture was stirred. After the mixture was stirred for 2 hours, the resulting reaction mixture was washed with a 10% sodium carbonate aqueous solution and saturated brine, and dried over magnesium sulfate. After separation by filtration, the solvent was distilled off using an evaporator. Consequently, 0.42 g of crude β-methacryloyloxy-β-methyl-γ-butyrolactone represented by formula (8) was obtained, and a quantitative isomerization reaction was confirmed by HPLC and NMR.

(8)

Example 3

Synthesis of α,α,β-trimethyl-β-methacryloyloxy-γ-butyrolactone (compound in which $R_1$, $R_2$, $R_5$, $R_6$=methyl, and $R_3$, $R_4$=hydrogen)

In a 1 L four-necked flask, 100 g of 2-oxopropyl methacrylate obtained by the method in Example 1, 800 g of ethyl acetate and 50 mg of p-methoxyphenol were put, and a stirrer, a thermometer, a Dimroth cooling tube and a gas inlet tube were connected thereto. The resulting solution was stirred and cooled to about 5° C. using an ice bath, and 0.3 equivalent of a diethyl ether complex of boron trifluoride was added thereto based on a substrate. While liquid temperature was kept at about 5° C. under stirring, a dimethylketene gas generated as gas for blowing with a nitrogen gas into an ethyl acetate solution in which isobutyryl chloride (made by ALDRICH Corporation, purity: 98%) and triethylamine are mixed was passed to the solution through a gas inlet tube at a rate of 0.2 equivalent/h based on the substrate, and the reaction was continued until 2-oxopropyl methacrylate disappeared by GC analysis. The reaction ended in 10 hours, blowing of the dimethylketene gas was stopped, and the remaining dimethylketene was removed to an outside of the system by passing the nitrogen gas.

The resulting reaction mixture was washed with a 10% sodium hydrogen carbonate aqueous solution and saturated brine, and dried over anhydrous magnesium sulfate. After separation by filtration, 50 mg of p-methoxyphenol was added thereto, and the solvent was distilled off using an evaporator. The reaction mixture after the solvent was distilled off was recrystallized twice using toluene and heptane to give 63.8 g of α,α,β-trimethyl-β-methacryloyloxymethyl-β-propiolactone having a purity of 99.5% according to HPLC analysis (yield: 53.1% based on 2-oxopropyl methacrylate).

Figure 2:
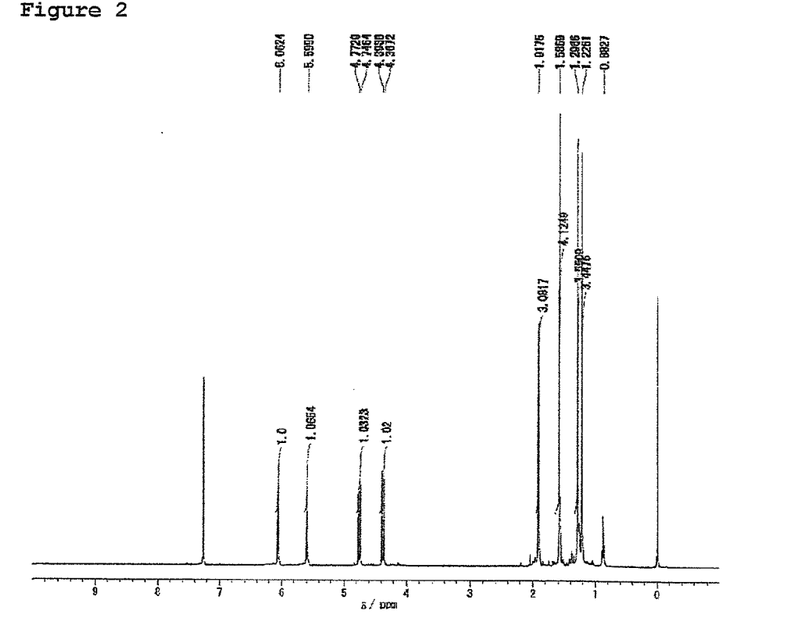
FIG. 2 shows an NMR spectrum of α,α,β-trimethyl-β-methacryloyloxy-γ-butyrolactone obtained by a method in Example 3.

In a 50 mL four-necked flask, 0.5 g of α,α,β-trimethyl-β-methacryloyloxymethyl-β-propiolactone was put, and dissolved in 10 g of ethyl acetate, and a stirrer, a thermometer and a Dimroth cooling tube were connected thereto. Further, 5 mol % of diethyl ether complex of boron trifluoride was added thereto based on the substrate, and 5 mg of p-methoxyphenol was added thereto, and while solution temperature was kept at 30° C., the resulting mixture was stirred. After the mixture was stirred for 2 hours, the resulting reaction mixture was washed with a 10% sodium carbonate aqueous solution and saturated brine, and dried over magnesium sulfate. After separation by filtration, the solvent was distilled off using an evaporator. A quantitative isomerization reaction to crude α,α,β-trimethyl-β-methacryloyloxy-γ-butyrolactone represented by formula (9) was confirmed. FIG. 2 shows an NMR measurement chart.

(9)

Example 4

Synthesis of β-methacryloyloxy-γ-butyrolactone (compound in which $R_1$=methyl, and $R_2$, $R_3$, $R_4$, $R_5$, $R_6$=hydrogen)

In a 2 L four-necked flask, 180 g of potassium methacrylate (made by Wako Pure Chemical Industries Ltd., purity: 98.0%) was put, and 900 g of N,N-dimethylformamide was added thereto, and a stirrer, a thermometer and a Dimroth cooling tube were connected thereto. Then, 308 g of 2-bromo-1,1-diethoxyethane (made by ALDRICH Corporation, purity: 97%), 0.9 g of p-methoxyphenol and 1.32 g of tetramethylammonium iodide were added thereto, and the resulting mixture was allowed to react for 2 hours at 150° C. under stirring. The reaction mixture was cooled to room temperature, a precipitate was separated by filtration, and then N,N-dimethylformamide was distilled off, and the resulting product was distilled under reduced pressure to obtain 174 g of a reaction product (GC purity: 98.5%). From the thus obtained reaction product, 19 g was put into a 1 L four-necked flask subjected to replacement with nitrogen, stirred and dispersed into 430 mL of water, and 0.21 g of hydroquinone, 0.41 g of 1-phenyl-3-pyrazolidinone (made by Tokyo Kasei Kogyo Co., Ltd., purity: 98.0% or more) and 2.8 g of 85% phosphoric acid were added thereto, and the resulting mixture was allowed to react at 70 to 80° C. for 3 hours under stirring. The reaction mixture was cooled to room temperature, and neutralized using a 10% sodium hydrogen carbonate aqueous solution, and repeatedly extracted with diethyl ether. An organic layer was dried over magnesium sulfate, separated by filtration, and distilled under reduced pressure to give 5.6 g of 2-oxoethyl methacrylate (yield: 27.6% based on potassium methacrylate).

In a 200 mL four-necked flask subjected to replacement with nitrogen, 5.0 g of 2-oxoethyl methacrylate and 50 g of toluene were put, and a stirrer, a thermometer, a Dimroth cooling tube and a gas inlet tube were connected thereto. After the solution was stirred and solution temperature was adjusted to about 10° C. using a water bath, 4.5 mol % of diethyl ether complex of boron trifluoride was added thereto based on a substrate. While solution temperature was kept at about 10° C. under stirring, a ketene gas was passed to the solution through the gas inlet tube at a rate of 2.1 equivalent/h based on the substrate, and the reaction was continued until a decrease of a 2-oxoethyl methacrylate peak stopped by GC analysis. After 90 minutes, blowing of the ketene gas was stopped, and the remaining ketene was removed to an outside of the system by passing a nitrogen gas.

The resulting reaction mixture was washed with a 10% sodium carbonate aqueous solution and saturated brine, and dried over magnesium sulfate. After separation by filtration, 0.2 g of hydroquinone was added thereto, and the solvent was distilled off using an evaporator to obtain 3.4 g of crude β-methacryloyloxymethyl-β-propiolactone.

Figure 3:
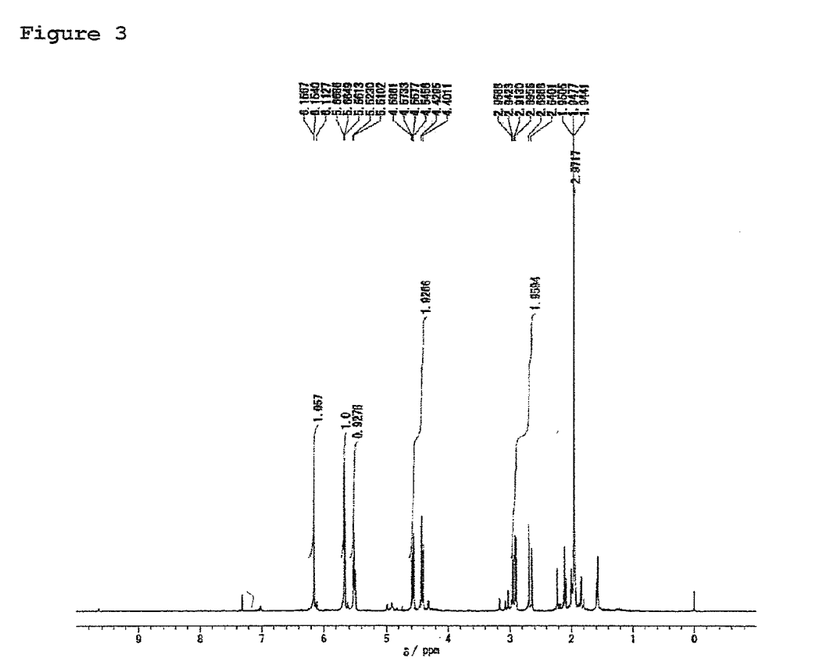
FIG. 3 shows an NMR spectrum of β-methacryloyloxy-γ-butyrolactone obtained by a method in Example 4.

In a 20 mL Schlenk flask, 2.0 g of crude β-methacryloyloxymethyl-β-propiolactone was put, and dissolved in 8.0 g of toluene. Further, 54 μL of diethyl ether complex of boron trifluoride was added thereto, and the resulting mixture was warmed to 30° C. and stirred. After the mixture was stirred for 2 hours, the resulting reaction mixture was washed with a 10% sodium hydrogen carbonate aqueous solution and saturated brine, and dried over magnesium sulfate. After separation by filtration, the solvent was distilled off using an evaporator to give 1.1 g of crude β-methacryloyloxy-γ-butyrolactone represented by formula (10). FIG. 3 shows an NMR measurement chart.

(10)

Example 5

Synthesis of β,γ-dimethyl-β-methacryloyloxy-γ-butyrolactone (compound in which $R_1$, $R_2$, $R_3$=methyl, and $R_4$, $R_5$, and $R_6$=hydrogen)

In a 2 L four-necked flask subjected replacement with nitrogen, 150 g of 3-hydroxy-2-butanone (made by Tokyo Chemical Industry Co., Ltd., purity: 95.0% or more) was put, and dissolved in 750 g of methylene chloride, and a stirrer, a thermometer and a Dimroth cooling tube were connected thereto. After the solution was stirred and cooled to about 5° C., 190 g of triethylamine and 80 mg of p-methoxyphenol were added thereto. While the solution was cooled to about 5° C. under stirring, 178 g of methacryloyl chloride was slowly added dropwise thereto over 4 hours, and further stirred for 30 minutes after completion of the dropwise addition to allow a reaction. The resulting reaction mixture was washed with 1 N-hydrochloric acid, a 10% sodium carbonate aqueous solution and saturated brine at room temperature, dried over anhydrous magnesium sulfate and separated by filtration to obtain a reaction crude liquid. The solvent of the reaction crude liquid was distilled off using an evaporator, 80 mg of p-methoxyphenol was added thereto and the resulting solution was distilled under reduced pressure to give 141 g of 3-oxobutane-2-yl methacrylate of 96.5% GC purity (yield: 53.1% based on 3-hydroxy-2-butanone).

In a 1 L four-necked flask, 200 g of 3-oxobutane-2-yl methacrylate was put, and 460 g of ethyl acetate was added thereto and the resulting mixture was stirred to adjust a solution, and a stirrer, a thermometer, a Dimroth cooling tube and a gas inlet tube were connected thereto. After the solution was stirred and solution temperature was adjusted to about 30° C. using a water bath, 5.6 mol % of diethyl ether complex of boron trifluoride was added thereto based on a substrate. While solution temperature was kept at 30° C., a ketene gas was passed to the solution through the gas inlet tube at a rate of 0.55 equivalent/h based on the substrate, and the reaction was continued until 3-oxobutane-2-yl methacrylate disappeared by GC analysis. The reaction ended in 4.5 hours, blowing of the ketene gas was stopped, and the remaining ketene was removed to an outside of the system by passing a nitrogen gas.

Figure 4:
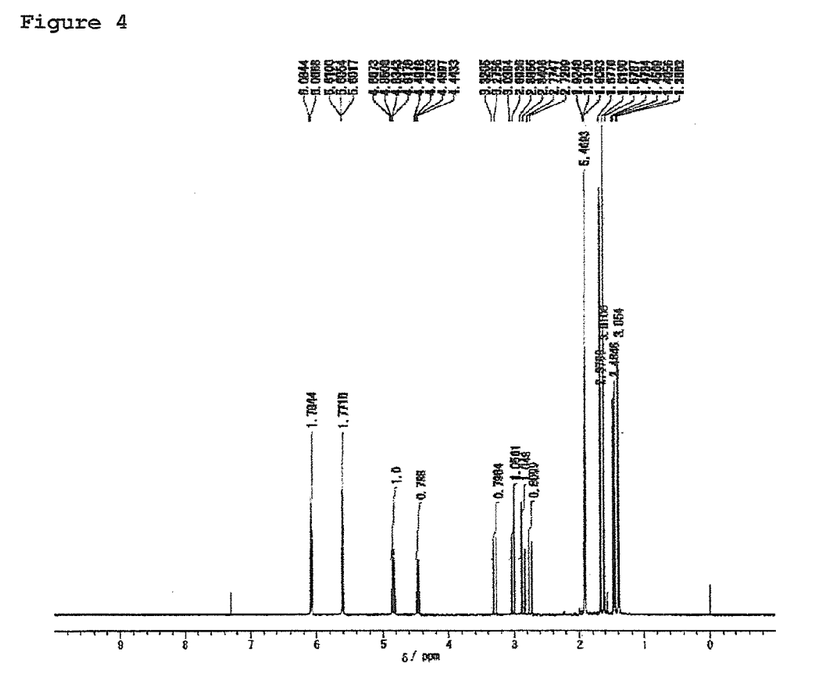
FIG. 4 shows an NMR spectrum of β,γ-dimethyl-β-methacryloyloxy-γ-butyrolactone obtained by a method in Example 5.

The resulting reaction mixture was washed with a saturated aqueous solution of sodium hydrogen carbonate and 10% brine. The organic layer obtained was dried over magnesium sulfate, magnesium sulfate was separated by filtration, and then the solvent was distilled off using an evaporator. To the reaction mixture after the solvent was distilled off, p-methoxyphenol was added, and the resulting solution was distilled under reduced pressure to give 103.8 g of β,γ-dimethyl-β-methacryloyloxy-γ-butyrolactone according to formula (11) and having a purity of 98.4% by HPLC analysis (yield: 40.9% based on 3-oxobutane-2-yl methacrylate). FIG. 4 shows an NMR measurement chart.

(11)

INDUSTRIAL APPLICABILITY

A β-(meth)acryloyloxy-γ-butyrolactone compound is a material that can be widely used for a resist material, an optical material, a coating material, a laminate material and so forth, and industrial use thereof will be promoted by the present manufacturing method. In particular, the compound is usefully applied as a photoresist material to be used in a process for manufacturing a semiconductor device or the like. Moreover, a new β-(meth)acryloyloxy-γ-butyrolactone compound can be supplied by applying the present manufacturing method, and the compound can be used in various ways, such as the resist material, the optical material, the coating material and the laminate material to be used in a process for manufacturing a printed circuit board, a liquid crystal display panel, a semiconductor device or the like.

What is claimed is:

1. A method for manufacturing a β-(meth)acryloyloxy-γ-butyrolactone compound represented by formula (2), wherein a methacrylate compound as represented by formula (3) and a ketene compound represented by formula (4) are condensed to form a methacrylate compound having the β-propiolactone skeleton represented by formula (1), and the resulting methacrylate compound having the β-propiolactone skeleton represented by formula (1) is isomerized to obtain the β-methacryloyloxy-γ-butyrolactone compound represented by formula (2):

(1)

(2)

(3)

(4)

wherein forming the methacrylate compound having a β-propiolactone skeleton as represented by formula (1) comprises:

dissolving the methacrylate compound as represented by formula (3) in an organic solvent to obtain a solution;

adding a catalyst in the solution, wherein the catalyst is diethyl ether complex of boron trifluoride;

passing the ketene compound represented by formula (4) to the solution and reacting at a temperature range of 0 to 50° C. to obtain the methacrylate compound having a β-propiolactone skeleton as represented by formula (1) in a reaction mixture;

washing the reaction mixture with a 10% sodium carbonate aqueous solution and saturated brine;

allowing the methacrylate compound having a β-propiolactone skeleton as represented by formula (1) to undergo isomerization through the help of the catalyst at a temperature range of 20 to 50° C.; and removing the organic solvent, so as to obtain the β-methacryloyloxy-γ-butyrolactone compound represented by formula (2), wherein, $R_1$ is hydrogen or methyl, and $R_2$, $R_3$, $R_4$, $R_5$ and $R_6$ are independently hydrogen or alkyl having 1 to 5 carbons.

2. The method for manufacturing the β-(meth)acryloyloxy-γ-butyrolactone compound according to claim 1, wherein a reaction for forming the (methacrylate compound having the β-propiolactone skeleton as represented by formula (1) and an isomerization reaction for isomerizing the resulting methacrylate compound having the β-propiolactone skeleton to form the β-methacryloyloxy-γ-butyrolactone compound represented by formula (2) are carried out as one-pot reactions.

* * * * *